United States Patent [19]

Kasper et al.

[11] 4,284,081
[45] * Aug. 18, 1981

[54] URINARY RETENTION CATHETER

[76] Inventors: Richard F. Kasper, 104 Sentry Hill Rd., Monroe, Conn. 06468; Joseph R. Carvalko, R.D. 1 Redwood Dr., Bethel, Conn. 06801

[*] Notice: The portion of the term of this patent subsequent to Apr. 10, 1998, has been disclaimed.

[21] Appl. No.: 16,350

[22] Filed: Mar. 1, 1979

Related U.S. Application Data

[63] Continuation of Ser. No. 755,259, Dec. 29, 1976, Pat. No. 4,148,319.

[51] Int. Cl.³ ............................................. A61M 25/00
[52] U.S. Cl. .................................. 128/349 B; 128/343
[58] Field of Search .............................. 128/348–350, 128/240–241, 246, 341, 343, DIG. 9

[56] References Cited

U.S. PATENT DOCUMENTS

| | | | |
|---|---|---|---|
| 3,385,300 | 5/1968 | Holter et al. | 128/348 |
| 3,421,509 | 1/1969 | Fiore | 128/349 R |
| 3,459,189 | 8/1969 | Alley et al. | 128/347 |
| 3,631,848 | 1/1972 | Muller | 128/348 X |
| 3,807,408 | 4/1974 | Summers | 128/349 R |
| 3,866,599 | 2/1975 | Johnson | 128/348 X |

Primary Examiner—Dalton L. Truluck
Attorney, Agent, or Firm—Martin D. Wittstein

[57] ABSTRACT

Disclosed is an improved drainage catheter for insertion into and retention in the bladder of the human body, and a novel stylet for use in inserting the catheter through the urethra and into the bladder. The catheter is formed of an elongate flexible cannula having a free and unobstructed open end adapted to be inserted into the bladder to permit drainage of waste material from the bladder and to facilitate the insertion of diagnostic instrumentation into the bladder. The end of the catheter in the bladder can expand to widen the opening and cause the open end to lie lower in the bladder. The stylet is an elongate flexible member adapted to be inserted into the cannula prior to the cannula being inserted into the urethra. The cannula and the stylet have cooperating stop means to prevent the stylet from passing through the cannula beyond a predetermined point so that the stylet can be used to push the cannula through the urethra and insert the open end into the bladder. The stylet has a rounded top which protrudes beyond the open end of the cannula to provide a guide for the cannula in passing through the urethra so as to prevent trauma thereto, the tip being removable so that a cleaning brush element can be attached to the stylet. The cooperating stop means can be arranged such that the cannula will defect at the stop means on the cannula so that the stylet moves freely to provide an indication that the catheter is properly located and secured within the bladder.

3 Claims, 9 Drawing Figures

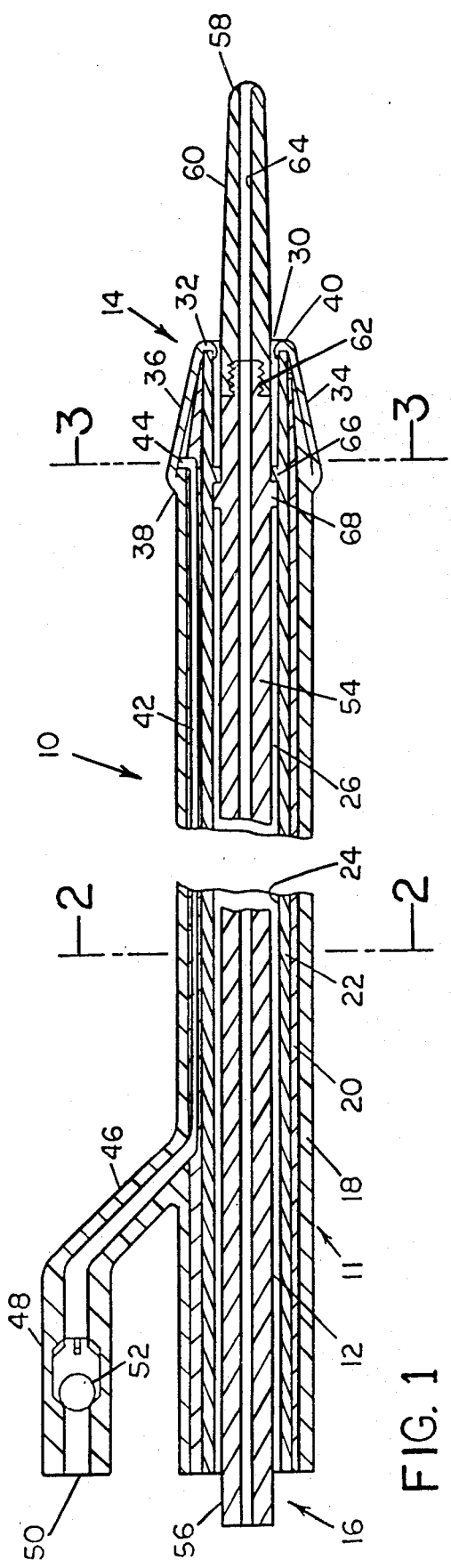
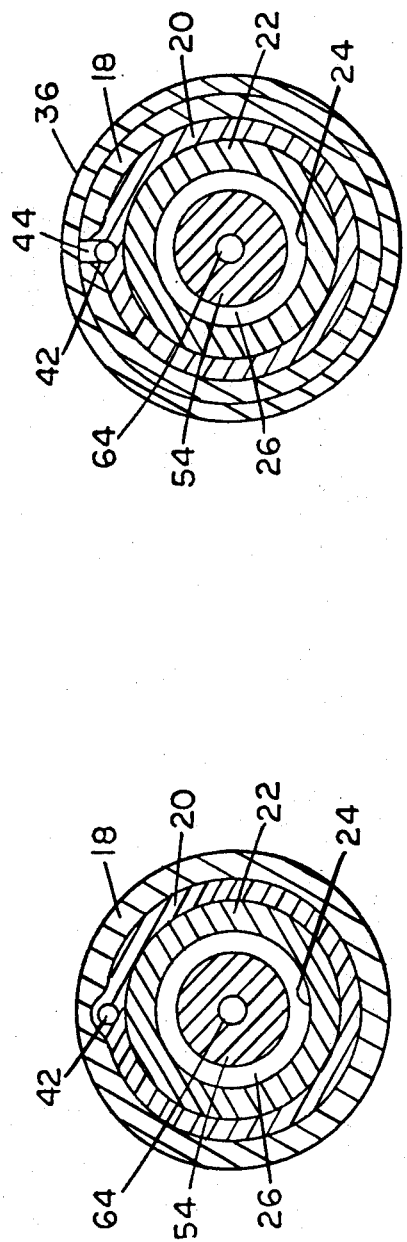
FIG. 1
FIG. 2
FIG. 3

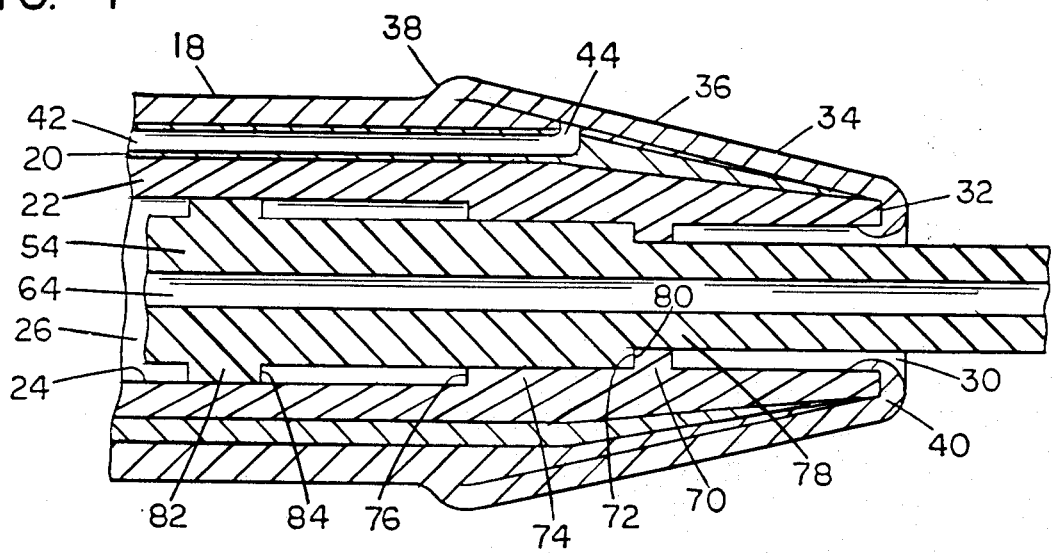
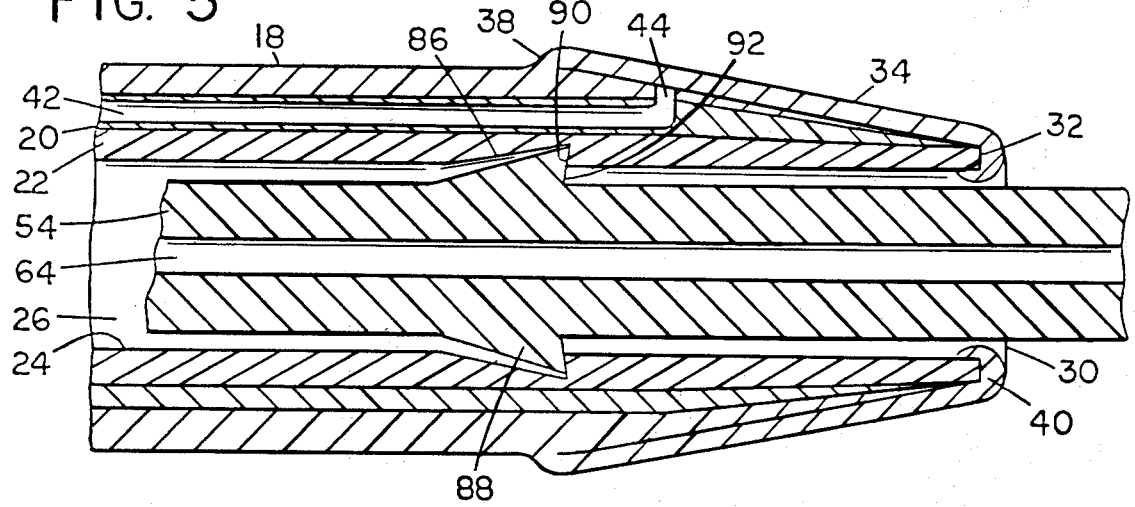
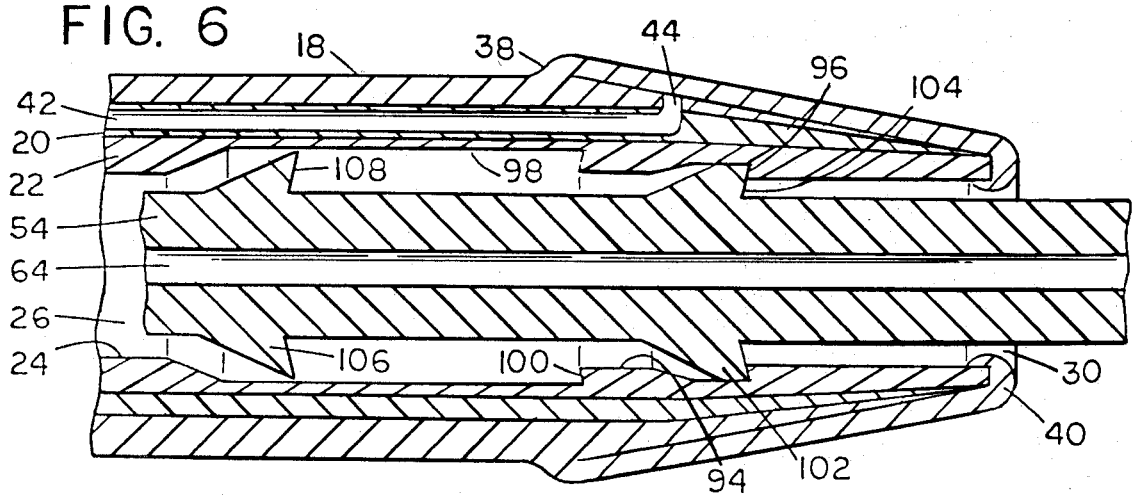

URINARY RETENTION CATHETER

This is a continuation of application Ser. No. 755,259 filed Dec. 29, 1976, now U.S. Pat. No. 4,148,319, issued Apr. 10, 1979.

BACKGROUND OF THE INVENTION

1. Field of the Invention

It is well recognized in the field of Urology that persons lose control of their urinary function. This loss of control may be temporary or permanent, depending upon the cause of the loss of urinary function. Temporary loss may be caused by a disease entity which is curable by medical or surgical treatment, whereas permanent loss of control may be caused by an incurable disease entity or physical trauma resulting in partial or total paralysis of the muscles which cause normal urination. The bladder is a dome shaped container with muscular walls and which accepts urine from the kidneys for temporary storage. During normal voluntary urination, the muscles in the bladder wall contract and simultaneously the sphincter muscle surrounding the opening in the bladder which communicates with the urethra relaxes so that the urine stored in the bladder is released into the urethra and expelled from the body.

The causes for loss of normal voluntary control of the urination process are manifold and the consequences are indeed severe. If urine cannot be periodically expelled from the bladder, the urine becomes stagnant and bacteria multiply at an exceedingly rapid rate, resulting in infection of the bladder. Chemical changes in the urine due to the infection cause painful urination and can also cause general dibilitation of health. If, after infection occurs, the urine retention is still permitted to continue for any considerable length of time beyond normal voluntary urination frequency, ascending infection can occur, that is the infection in the bladder spreads to the ureters and to the kidneys, thereby causing still more serious consequences, such as failure of one or both of the kidneys to function. If the kidneys do not function to cleanse the blood of impurities and form urine, uremia results and death occurs in the absence of the availability of recently developed artificial kidney machines. If, on the other hand, the kidneys continue to function and fill the non-draining bladder with urine, the bladder can burst, thereby emptying the bacteria laden urine into the abdominal cavity. The usual result of this is peritonitis, which is an inflammation of the peritoneum, the membrane that lines the abdominal cavity, and the results of inflammation of this membrane are always serious. The time between the occurrence of acute peritonitis and death may be only a matter of a few hours to a few days depending upon the severity of the infection. Septicemia, an infection of the blood, is another serious consequence of excessive retention of urine in the bladder, since the bacteria in the bladder, ureters and kidneys invades the blood through the minute blood capillaries in these organs.

Obviously other complications, bodily disorders and disfunctions and serious consequences, too numerous to mention herein, can result from failure of proper urination. It is obvious that constant periodic drainage of the bladder to eliminate urine and other body waste material is essential not only to good health but to maintaining life itself.

Techniques of treatment for loss of normal voluntary control of the urination process are relatively few in number. Depending on the nature of the cause, a superpubic technique involving surgery may eliminate the drainage problem in some circumstances. Since surgery is involved, this treatment is traumatic and severe, and is utilized only when absolutely necessary. Drug therapy is effective in some cases to promote drainage of the bladder, but due to the relatively few causes of loss of voluntary control which will respond to drugs and the ever presence of undesirable side effects, drug therapy is considered to be a relatively ineffective method of dealing with the problem.

2. Necessity for Practice of Invention

Since the loss of voluntary control over the urinary function is typically a secondary effect caused either by disease or trauma, it has become a well established medical practice to relieve the urinary drainage problem mechanically by means of the process of catheterization. If the primary cause of the loss of voluntary urination control is from a curable disease, the catheterization process is maintained on a temporary basis only for so long as necessary until voluntary control returns. If the cause of loss of control is permanent, as in the case of paralysis such as with paraplegics and quadriplegics, the catheterization process must be maintained on a permanent basis in order to maintain life.

In the catheterization process, a tube or catheter is inserted into and through the urethra until the remote or distal end is located within the bladder, usually being disposed just past the sphincter muscle at the juncture of the bladder with the urethra. The near or proximal end of the tube remains outside of the body and there is thus provided a path or channel through which urine in the bladder can drain as the need arises. Once a catheter has been passed through the urethra and inserted into the bladder, it is generally necessary, in connection with the disease and trauma conditions described above, to have the catheter retained in the urinary tract with the distal end of the catheter in the bladder, such retention being in the order of several days to several weeks without removal. Catheters which are designed for use a function are called urinary retention catheters and are typically provided by including an inflatable balloon at the distal end of the catheter which is deflated during insertion of the catheter and which is inflated by passing a fluid, typically water or saline solution through a passage within the catheter, called an inflation lumen. Thereafter, fluid from the bladder drains through the main passage of the catheter, called the drainage lumen.

3. Problems of Catheterization

Inserting a catheter into the urethra can be a painful and traumatic experience, the degree of pain and trauma depending on the construction of the catheter being inserted, the technique for inserting it, and the experience and the skill of the person performing the insertion whether that person is the doctor or other individual. Since the designers of catheters have no control over the last named characteristic, the present invention has been developed with the first two characteristics principally in mind, but also with consideration for the fact that the catheter may on many occasions be inserted by other individuals who would not be as skilled as the doctor. The reason for possible pain and trauma is that the urethra, whether male or female, is a relatively tortuous tube of varying cross-sectional dimensions and is normally collapsed along most of its length. The upper portion of the urethra is provided with sphincters or valves which it enters the bladder neck. The female urethra is somewhat shorter and straighter than the male urethra but otherwise both are much the same. The urethra is a very delicate organ and cannot withstand any appreciable amount of lateral pressure against the urethral wall without causing some degree of rupture. Since the urethra has a high concentration of pain sensing nerve endings, any distortion, whether of change in size or shape, is very uncomfortable at the least and usually painful, and any trauma to the urethra is accompanied by a great deal of pain. It is not uncommon for the patient to have to be anesthetized in order to insert many common urinary catheters. In addition to the pain, bacteria in the urethra can enter the blood stream if the urethra is traumatized, with the same result discussed above in connection with rupture of the bladder.

Extensive research and development have been carried out over a long period of time in the design of catheters, and a large number of different catheter designs appear in the medical and patent literature. The reason for this is that design characteristics for urinary drainage catheters are highly conflicting from the standpoints of patient discomfort and functionalism. In order to reduce the probability of trauma and resulting pain to the urethra as well as discomfort to the patient during long periods of retention, a urinary drainage catheter should be as thin as possible, highly flexible and pliant, and have a soft rounded end. From the functional standpoint, on the other hand, the catheter must be of sufficiently thick and rigid construction that it will not buckle while being passed through the urethra, it should have as wide a drainage opening and lumen as possible to promote complete drainage and prevent clogging, and the end should be free and unobstructed in order to facilitate the use of the catheter as an aid to the insertion of diagnostic and treatment instrumentation into the bladder. Of great importance is the fact that a retention catheter must have an effective means for retaining the catheter in place in the bladder which will not obstruct either the flow of urine or substantially the complete drainage of urine therefrom, but at the same time has sufficient retaining capability that a patient, particularly a senile patient, cannot forcibly pull the catheter out of the bladder and into the urethra thereby causing extreme damage thereto. Further, any urinary drainage catheter must be formed of a material totally inert to the effects of urine and other waste materials, be capable of absolute sterilization, and be manufacturable to strict tolerances, in high volume and at low cost considering the disposable nature of the product. Still other criteria may be apparent to those skilled in the art.

4. The Prior Art

In view of the foregoing diverse criteria, the basic design of commercially available retention catheters has changed very little over the past half century, and the well known Foley retention catheter is almost universally used by doctors, hospitals, nursing homes, etc. to alleviate loss of voluntary bladder control U.S. Pat. Nos. 2,892,458; 2,936,761; 3,292,627 and 3,394,705 are mentioned as illustrating typical prior art catheters which are usually formed of relatively thick walled construction so as to be insertable without buckling, have a rounded solid tip to prevent trauma to the delicate lining of the urethra, and have side openings adjacent the tip to communicate the interior of the bladder with the drainage lumen. The prior art catheters also have an inflatable balloon portion beyond the drainage opening in order to retain the catheter in place. These catheters, and many more like them, are undesirable from the standpoint that considerable pain may be experienced in introducing a relatively wide, semi-rigid catheter into a relatively narrow urethra. Further, the small side openings can easily clog from clots of sediment material which collects in the bottom of the bladder. Still further, as a result of the solid tip, it is impossible to pass diagnostic or treatment instrumentation through the catheter for the purpose of inspecting or treating the interior of the bladder. The capability of inserting instrumentation through the catheter after it is in place is very important in the urological practice since prior treatment involves the use of anesthesia in order to insert steel tube instrumentation as has been the practice.

In U.S. Pat. No. 2,677,375, recognition was given to the desirability of removing the fixed rounded tip so as to provide a drainage opening adjacent the inflatable retention balloon. Strips are provided across the opening for engagement by an inserting stylet. This construction is disadvantageous in that the strips are likely to obstruct the passage of sediment clots and thus clog the drainage opening, and even more harmful is the fact that the insertion of such a blunt end as is apparent in this device is almost certain to cause considerable trauma to the delicate wall of the urethra. It is also apparent that it would be at least difficult, if not impossible, to pass instrumentation through this catheter in view of the strips across the open end. Such a device would be wholly unacceptable to the urological practitioner.

A significant aspect of the present invention is the provision of an improved stylet which is utilized both during insertion of the catheter through the urethral passage and thereafter as a cleaning implement. U.S. Pat. Nos. 2,118,631; 2,164,926 and 2,856,934 are cited as representative of prior art stylets which are utilized solely to assist in inserting the catheter, the first two being of the typical push rod type and the third being of the filiform type. Although the use of a stylet to insert the catheter obviates the problem of bucking of the catheter during insertion and thereby permits the catheter to have a relatively thin wall construction, the push rod type used in conjunction with a closed end catheter is undesirable from the standpoint that there is no way of accurately ascertaining when the end of the catheter enters the bladder because the stylet blocks the drainage opening or the drainage lumen or both. The filiform device is undesirable because of the possibility of injuring the delicate wall of the urethral passage during the insertion of the filiform unless great care is exercised because of the fact that the filiform is of necessity very thin and therefore must be relatively rigid and sharp nosed. Other disadvantages of this technique for inserting drainage catheters will be apparent to those skilled in the art.

Another significant improvement of the present invention is the novel construction of the inflatable retention balloon to cause the open end of the catheter to expand and widen, which assists in drainage and in retention. Some consideration has been given to this problem as evidenced by U.S. Pat. No. 2,892,458 mentioned above, as well as by U.S. Pat. Nos. 3,438,375 and 3,889,686. In the first patent, the balloon is constructed to be less inflatable adjacent the lateral drainage opening through the catheter wall so that the balloon cannot overlie and block the opening if the catheter tends to settle in the bladder or is pulled by the patient. In U.S.

Pat. No. 3,438,375, the opposite theory is applied and the balloon is constructed to purposely overlie the lateral drainage but be spaced therefrom so that the delicate lining of the bladder cannot be drawn into the opening by sub-atmospheric pressure. In U.S. Pat. No. 3,889,686, a lateral opening is provided below the balloon as well as above so as to promote better drainage. All of these techniques have inherent disadvantages in that they present design problems which are difficult to overcome in manufacturing the catheter, they are not nearly as effective in practice as eliminating the lateral drainage opening altogether so that the inflation balloon presents no interference problem whatever, and they cannot function to allow movement of a stylet to indicate when the balloon is inflated because the rounded tip closes the longitudinal end of the drainage lumen.

SUMMARY OF THE INVENTION

The present invention substantially obviates if not completely eliminates many of the disadvantages of prior art and commercially available urinary retention catheters and also provides advantages and desirable features not heretofore obtainable with such catheters.

The principles of the present invention are embodied in a novel urinary drainage catheter, a novel stylet for use with the catheter and in a novel cooperation in the combination of the catheter and the stylet together.

In general, the catheter comprises an elongate cannula formed preferably although not necessarily of a plurality of layers of flexible and pliant materials, the inner and outer layers being of relatively soft latex rubber and an intermediate layer being of relatively thinner but stronger silicone rubber. The cannula has both distal and proximal ends, the length of the cannula being such that the distal end is disposed within the bladder and the proximal end is disposed exteriorly of the urethra when the catheter is in operative position in the body. The cannula has an inner tubular wall surface defining a drainage lumen which extends from the distal end substantially to the proximal end. The distal end is open and unobstructed so as to communicate the interior of the bladder directly with the full cross-sectional area of the drainage lumen. There is means on the inner tubular wall adjacent the distal end which defines a portion of the drainage lumen of slightly different diameter than the diameter of the rest of the drainage lumen, which means forms an abutment for the stylet used to insert the catheter. The catheter also includes an expandable means preferably in the form of an inflatable balloon connected to the inner and outer layers of the cannula adjacent the distal end for retaining the distal end in the bladder and for expanding the distal end of the cannula so as to widen the opening and to dispose the end of the cannula lower in the bladder than it is with the balloon uninflated. In one embodiment, the abutment forming means forms a hinge about which the distal end expands and the abutment means distorts to a shape which allows the stylet to pass beyond the abutment means and move freely back and forth for at least a limited distance, thereby providing an indication that the balloon has inflated.

The stylet comprises generally an elongate flexible body member of substantially uniform diameter throughout a major portion of its length. Adjacent one end of the body member is means defining a portion of different diameter than the diameter of the body member and defining an abutment surface adapted to engage with the abutment means disposed in the cannula when the stylet is inserted therein. The stylet is provided with a tapered tip element on the end adjacent the abutment surface, the tip element having a relatively smooth rounded end. The tip element is removably connected to the end of the body member so that it can be removed from the body member after the stylet is withdrawn from the catheter, and a brush element is provided which is connectable to the body member for cleaning the catheter. Both the body member and the tip element have a central bore of relatively small diameter so that the flow of urine therethrough affords a positive indication that the distal end of the catheter has entered the bladder.

Having briefly described the general nature of the present invention, a principal object thereof is to provide a retention drainage catheter and stylet for use therewith which avoids the disadvantages of prior art constructions and provides advantages not heretofore attainable in devices of this nature.

Another object of the present invention is to provide a retention drainage catheter and stylet for use therewith which avoids to the fullest possible extent any likelihood of injury to the urethra during insertion of the catheter.

Another object of the present invention is to provide a retention drainage catheter and stylet for use therewith which is designed to render insertion relatively simple and with a minimum of discomfort so that the insertion process can be carried out without the need for anesthesia.

Another object of the present invention is to provide a retention drainage catheter and stylet for use therewith in which the catheter and stylet have a cooperating abutment relationship by which the stylet is used to insert the catheter into the bladder and which does not interfere with the free flow of urine or other waste materials through the catheter.

Another object of the present invention is to provide a retention drainage catheter and a stylet for use therewith in which the entire full width portion of the catheter is pulled through the urethra rather than a portion thereof being pushed therethrough.

Another object of the present invention is to provide a retention drainage catheter which is constructed to provide the widest possible drainage opening from the bladder directly into the drainage lumen of the catheter in order to minimize if not altogether prevent clogging of the drainage opening due to sediment material collecting in the bladder.

Another object of the present invention is to provide a retention drainage catheter through which various types of instrumentation may be passed into the bladder for performing diagnostic or treatment techniques therein.

Another object of the present invention is to provide a retention drainage catheter having a novel inflatable retention balloon construction which causes the distal end of the catheter to expand to provide a still wider drainage opening which lies lower in the bladder than with conventional retention catheters.

Another object of the present invention is to provide a retention drainage catheter in which expansion of the distal end of the drainage lumen is accomplished in a manner which allows at least limited free movement of the stylet to provide an indication that the balloon has properly inflated.

Another object of the present invention is to provide a stylet for use with a retention drainage catheter which provides a positive indication of when the end of the catheter has passed from the urethra into the bladder by permitting a limited flow of urine through the stylet.

Another object of the present invention is to provide a stylet for use with a retention drainage catheter in which the stylet is used as a cleaning implement for the catheter after the stylet is removed from the catheter and a brush element is substituted for a rounded tip element used during insertion of the catheter.

Another object of the present invention is to provide a retention drainage catheter and stylet for use therewith which is impervious to the effects of urine, is susceptible to complete sterilization and can be easily and inexpensively manufactured in large quantities.

These and other objects and advantages of the present invention will be more readily apparent from an understanding of the following detailed description of several preferred embodiments of the invention when considered in conjunction with the accompanying drawings in which:

FIG. 1 is a longitudinal sectional view of a retention drainage catheter and stylet for use therewith embodying, in one form, the principles of the invention;

FIG. 2 is an enlarged cross-sectional view taken on the line 2—2 of FIG. 1;

FIG. 3 is an enlarged cross-sectional view taken on the line 3—3 of FIG. 1;

FIG. 4 is an enlarged fragmentary view of the distal end of the catheter shown in FIG. 1 showing a modified form of abutment means between the catheter and the stylet;

FIG. 5 is an enlarged fragmentary view similar to FIG. 4 showing a further modified form of abutment means between the catheter and the stylet;

FIG. 6 is an enlarged fragmentary view similar to FIG. 4 showing a still further modified form of abutment means between the catheter and the stylet;

DETAILED DESCRIPTION OF THE PREFERRED EMBODIMENTS

Figure 7:
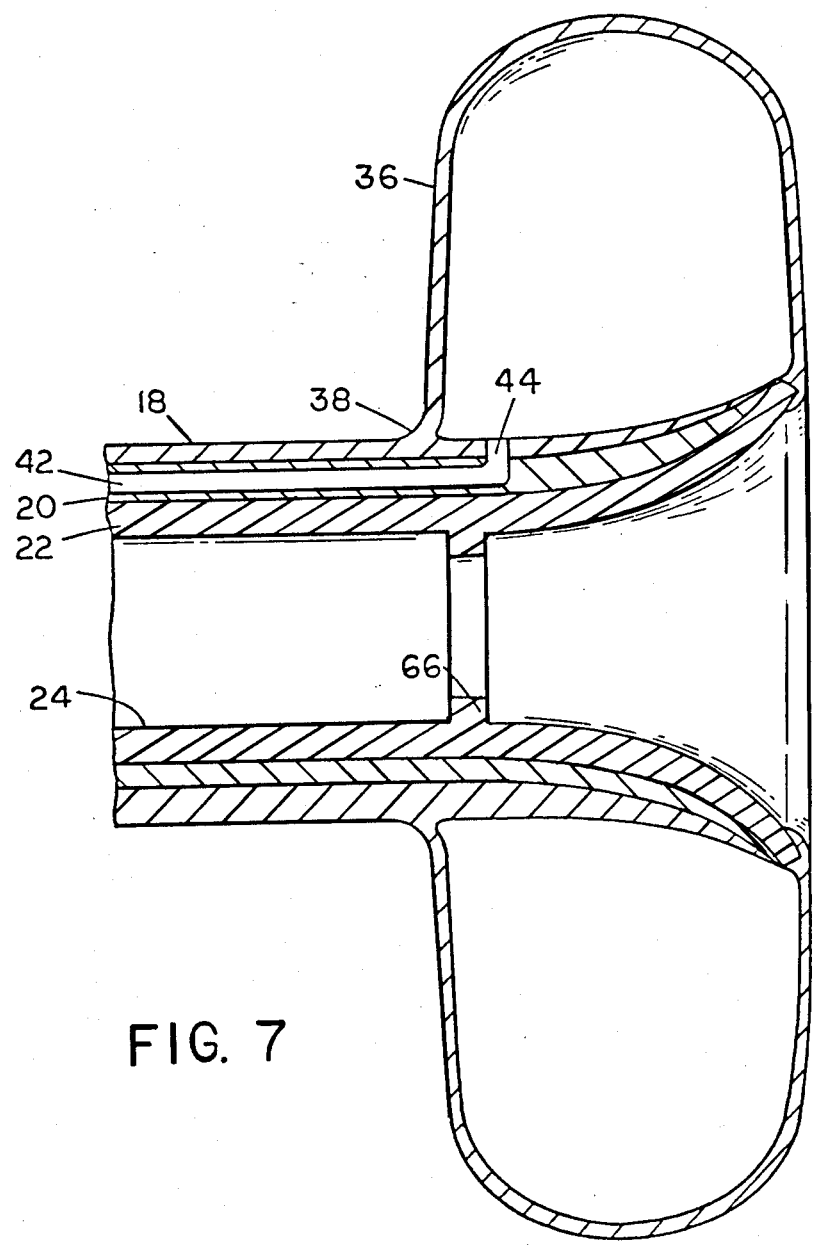
FIG. 7 is an enlarged fragmentary view of the embodiment of FIG. 1 showing the retention balloon in its inflated condition.

Referring now to the drawings and particularly to FIGS. 1-3 thereof, there is shown a retention drainage catheter and inserting stylet therefore in assembled relationship ready for use, the assembly being generally indicated by the reference numeral 10, the catheter and stylet being generally indicated by the numerals 11 and 12 respectively. The catheter has a distal end generally designated by the numeral 16, the length of the catheter being such that the distal end 14 can be fully inserted into the bladder while the proximal end still remains outside of the entrance to the urethra. The catheter 11 is constructed as a multi-layer cannula and has an outer layer 18 of relatively soft and pliant latex rubber which is selected to meet the physical requirements set forth above, but principally which must withstand the corrosive effects of urine and withstand the high temperatures of sterilization. An intermediate layer 20 of silicone rubber is disposed within the outer layer 18, the silicone rubber having greater strength than the latex rubber but otherwise meeting the same physical requirements as the latex rubber. Another layer 22 of latex rubber forms an inner layer disposed within the intermediate silicone layer, the inner wall 24 of the inner layer 22 defining a drainage lumen 26 through which urine drains from the bladder.

A principal feature of the present invention resides in the provision of a longitudinal drainage opening 30 at the distal end 14 of the catheter. In the conventional catheters, as shown in the prior art cited hereinabove, the catheter is provided with a rounded bullet shaped tip to facilitate insertion of the catheter through the urethra with a minimum of discomfort and risk of trauma, and a laterally opening drainage port is provided adjacent the tip of the catheter. In the present invention, however, the conventional tip has, in effect, been removed and the several layers of the cannula 11 terminate to define the longitudinal opening 30 which is open and unobstructed in order to communicate the interior of the bladder directly with the full cross-sectional area of the drainage lumen 26 rather than through a restricted lateral opening as in the prior art. The manner in which the layers of the cannula terminate to define the opening 30 is best seen in FIG. 4 wherein the inner latex rubber layer 22 terminates abruptly in an annular wall 32, whereas the intermediate silicone layer 20 and the outer latex layer 18 are both tapered and merge to points adjacent the distal end 14 of the cannula so as to define a smooth, gradually widening portion 34 of the cannula surface from the annular wall 32 to the widest portion of the cannula 11. The reason for this tapering portion is to provide a smooth, gradually expanding insertion portion of the catheter 11 which cooperates with a gradually widening portion of an inserting stylet to be hereinafter described. It will be apparent that the longitudinal opening 30 provides a wider and less obstructed access from the bladder into the drainage lumen than does the lateral openings in the prior art catheters.

The catheter 11 includes means for retaining the distal end 14 thereof within the bladder after the distal end has been passed through the urethra and has entered the bladder. Since the juncture of the bladder and the urethra is defined by a sphincter muscle which defines a relatively small opening even when the sphincter muscle is relaxed, it is possible to prevent removal of the catheter by providing the end thereof with an expandable means which overlies a small portion of the bottom of the bladder wall surrounding the sphincter. In the present invention, the preferred means for retaining the catheter in place is the inflatable balloon technique which is well known in the art but which is configurated in the present invention to cooperate in a novel manner with the specific construction of the distal end of the catheter to cause the distal end of the catheter to expand and partly overlie the bottom wall of the bladder. More particularly, the inflatable balloon is a relatively thin layer 36 of latex rubber which is integrally molded or suitably bonded to the outer layer 18 of the cannula at a point 38 downstream from the open end 30, the point 38 being selected to provide a balloon of suitable size to retain the catheter in place when the balloon is inflated. Although the balloon may vary in size depending on the location of the molded or bonded juncture 38, it is the practice to select a reasonable compromise in the size of the balloon based on two conflicting considerations. One is that the balloon should be as small as possible in order to place the drainage opening as close as possible to the sphincter muscle at the bottom of the bladder to facilitate substantially complete drainage of urine and sedimentary waste material in the bladder. The other consideration is that retention drainage catheters are very often used by elderly people who, for one reason or another, have lost voluntary control of the urinary function and the catheter must remain in place for extended periods of time. Due to senility or other factors of mental deterioration of the aged, many of these people have a tendency to try to pull the catheter out without realizing what they are doing, and as a consequence can cause themselves severe injury if the balloon is not large enough to retain the catheter in place even against substantial pulling force.

The present invention effectively aleviates both of the aforementioned problems by providing a retaining balloon designed to provide both maximum size for retention purposes and at the same time to keep the drainage opening close to the bottom of the bladder. The balloon layer 36 extends from the molded or bonded juncture 38 to the end of the cannula 11 and has an annular terminal portion 40 which encircles the annular wall 32 of the inner latex layer 18. The balloon layer 36 is separated from the outer layer 18 of the cannula from the juncture 38 to the annular wall 32 where the balloon layer is either integrally molded or suitably bonded to the annular wall 32 so as to form a fluid-tight seal therewith. It will be noted that the terminal portion 40 of the balloon layer 36 is thicker than the balloon layer and is smoothly rounded for ease of insertion as will more clearly appear hereinafter. In its non-inflated condition, the balloon layer lies flat on the tapered surface of the outer layer 18 and forms the gradually widening portion 34 of the cannula.

The balloon is inflated by means of an inflation lumen 42 formed in the silicone layer 20, the silicone layer being thicker in the area of the inflation lumen than the rest of the layer as best seen in FIGS. 2 and 3. With reference to FIG. 1, the inflation lumen 42 extends from a terminus 44 within the balloon layer 36 through the silicone layer 20 to a lateral extension 46 of the outer layer 18, the lateral extension terminating in a valve housing 48 and a fluid injection end 50. Any suitable valve member 52 is provided within the valve housing 48 to prevent the escape of the inflation fluid after the balloon layer 36 has been inflated. The silicon layer 20 is provided for the purpose of resisting any tendency of the inflation lumen 42 to expand into the drainage lumen 26 due to the pressure of the inflating fluid within the inflation lumen 42 and the balloon layer 36. Since the silicone rubber is stronger and less flexible than the latex rubber, it is desirable to maintain the silicone layer as thin as possible around its periphery and to thicken the silicone layer only at the location which surrounds the inflation lumen as shown in FIGS. 2 and 3.

The catheter assembly 10 includes a stylet 12 which is used to insert the catheter 11 into the urethra, and as a cleaning implement as will be more fully described hereafter. The stylet 12 is an elongated tube formed of a relatively rigid rubber or plastic material which meets the same physical characteristics as the material of the catheter with respect to being susceptable to sterilization, impervious to urine, etc. The stylet is sufficiently rigid so that it can be pushed through the urethra without buckling, and yet is also sufficiently flexible that it will conform somewhat to the configuration of the urethra during the insertion process, although a certain degree of straightening of the urethra during the insertion process is inherent in any catheterization process.

Figure 9:
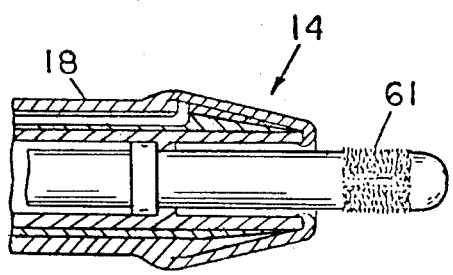
FIG. 9 is a view of a suitable brush cleaning element for use with the stylet.

The stylet 12 is formed as a rod 54 having a proximal end 56 and a distal end 58, the length of the rod between the ends 56 and 58 exceeding that of the catheter 11. The distal end is formed as a smooth rounded tip at the end of a tapered removable end portion 60 of the rod 54, the rod and the removable end portion being connected together by any suitable means such as the threads 62 or merely a press fit. The rounded end 58 and the taper on the end portion 60 facilitate a smooth sliding passage of the projecting end of the stylet through the urethra. The stylet is also provided with a longitudinal passageway or bore 64 which extends the entire length of the stylet and functions as a limited drainage passageway through which a small amount of urine can flow when the distal end of the stylet enters the bladder. This provides the person inserting the catheter with an indication of when the tip of the stylet enters the bladder, it being known how much further the catheter and stylet must be inserted into the urethra to dispose the distal end of the catheter in the bladder. The end portion 60 is replaced by a suitable brush element 61 such as that shown in FIG. 9 when it is desired to clean the drainage lumen 26.

The stylet and catheter are provided with cooperating abutment means by which the stylet pushes the catheter through the urethra as the stylet is manipulated through the urethra. In the embodiment shown in FIG. 1, an annular boss 66 is formed on the inner surface 26 of the inner latex layer, and a cooperating radial boss 68 is formed on the outer surface of the rod 54. The abutting engagement of the adjacent surfaces of the bosses 66 and 68 prevents the stylet from passing through the catheter and pulls the catheter through the urethra as the person inserting the catheter pushes on the stylet. It will be recognized that, although the annular boss 66 is formed of the relatively soft latex rubber, there is little likelihood that the radial boss 68 on the stylet will slip past the annular boss 66 during insertion of the catheter due to the fact that the tolerance relationships between the stylet and the catheter inside the drainage lumen 26 are very small, and the radial boss 68 is extremely close to, if not actually in sliding contact with, the inner wall 24 of the drainage lumen 26. It will also be noted that the boss 66 on the cannula is located substantially at the widest part of the gradually widening portion 34 of the cannula so that as the stylet pushes the catheter through the urethra, only the portion 34 is in advance of the abutting engagement between the catheter and the stylet. The advantage of this arrangement is that substantially the entire portion of the catheter which is not tapered is being pulled through the urethra with the result that there is no tendency for the catheter to buckle or slide back on the stylet during the insertion process.

Figure 8:
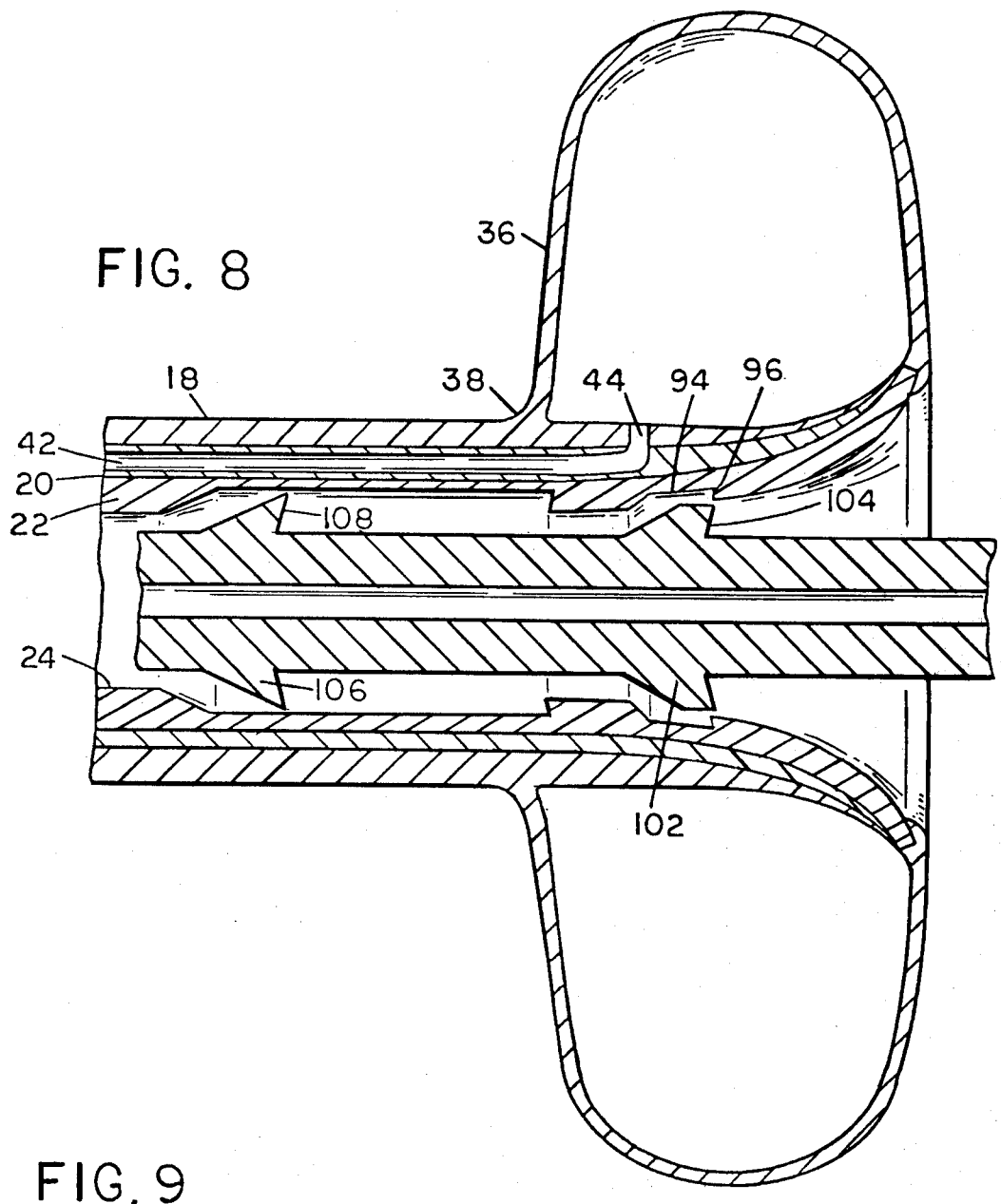
FIG. 8 is an enlarged fragmentary view similar to FIG. 7 of the embodiment shown in FIG. 6.

Three alternative embodiments of the abutment means between the catheter and stylet are shown in FIGS. 4–6. In FIG. 4 a multiple step abutment means is shown in which the inner layer 22 of the catheter is provided with an annular boss 70 which defines an abutment wall 72, and another annular boss or merely a portion 74 of the inner layer 22 of larger diameter from the rest of the inner layer defines another abutment wall 76 spaced rearwardly from the abutment wall 72. Correspondingly on the stylet, a radial boss or merely a portion 78 of the rod 54 which is of reduced diameter from the rest of the rod 54 defines an abutment wall 80, and a radial boss 82 defines another abutment wall 84 spaced rearwardly from the abutment wall 80. It will be observed that the two abutment walls 80 and 84 on the stylet are much more widely separated than the corresponding abutment walls 72 and 76 on the catheter, the reason for which will be made clear hereinafter. It will be apparent that if for any reason the forward abutment wall 80 should slip past the forward abutment wall 72 on the catheter, the rearward abutment wall 84 on the stylet will engage with the rearward abutment wall 76 on the catheter after the stylet has moved forwardly within the catheter a distance equal to the space between the rearward abutment wall 76 on the catheter and the rearward abutment wall 84 on the stylet. Thus, the plurality of abutment walls provides an added measure of safety against the stylet passing the single abutment means shown in FIG. 1 as well as another advantage discussed below in connection with the expansion of the inflatable balloon as shown in FIG. 8. It will be noted that the rear abutment wall 76 is located substantially at the widest portion of the gradually widening portion 34 of the cannula and the forward abutment wall 72 is located within the gradually widening portion 34 so that only the gradually widening portion of the cannula is pushed ahead of the abutment means during insertion of the cannula regardless of which of the above described pairs of abutment surfaces are in engagement with each other.

Another form of abutment means is shown in FIG. 5 in which the cooperating abutment surfaces formed on the catheter and stylet are in barb-like configuration to give an added measure of assurance against the stylet abutment surface slipping past the catheter abutment surface and failing to pull the catheter through the urethra. Thus, an annular recess 86 is formed on the inner surface 26 of the inner latex layer 22, and a cooperating radial boss or projection 88 is formed on the outer surface of the stylet rod 54. As shown in FIG. 5, the recess 86 is wedge shaped, and the projection 88 is correspondingly wedge shaped so that the recess has an abutment surface 90 and the projection has an abutment surface 92 which surfaces engage when the stylet is inserted into the drainage lumen 26 of the catheter. The abutment surfaces 90 and 92 are both slanted forwardly as they extend outwardly so that the recess 86 and projection 88 have a barb-like configuration. Although the diameter of the radial projection is larger than the diameter of the drainage lumen 26, as distinguished from the FIG. 1 and FIG. 4 embodiments where the stylet projections do not exceed the diameter of the drainage lumen 26, there is nevertheless no difficulty in inserting the stylet into the catheter since the inner latex layer 22 is relatively compressible, and the projection 88 simply compresses the material of the layer 22 as it moves through the drainage lumen 26 until the projection moves into the recess 86. In this embodiment of the invention, insertion of the stylet into the catheter is further facilitated by inserting the stylet from the distal end of the catheter rather than from the proximal end thereof as would be the direction of insertion for the embodiments shown in FIG. 1 and FIG. 4. It should be noted that insertion of the stylet in all of the disclosed embodiments is made easier by lubricating the stylet prior to insertion with any suitable sterile lubricant. For the same advantage as pointed out above in connection with the abutment means of FIG. 1, the abutment surfaces of the catheter and stylet are located adjacent the widest part of the gradually widening portion 34 of the cannula.

FIG. 6 shows another form of multiple step abutment means similar to that shown in FIG. 4 but having the abutment means configurated as shown in FIG. 5. The inner layer 22 of the catheter is provided with a forward annular recess 94 which defines an abutment surface 96 and another rearward annular recess 98 which defines another abutment surface 100 spaced rearwardly from the abutment surface 96. The stylet is provided with a forward radial projection or boss 102 which defines an abutment surface 104 for engagement with the abutment surface 96 and another rearward annular recess 98 which defines another abutment surface 100 spaced rearwardly from the abutment surface 96. The stylet is provided with a forward radial projection or boss 102 which defines an abutment surface 104 for engagement with the abutment surface 96 on the catheter and a rearward radial boss or projection 106 which defines another abutment surface 108 for engagement with the abutment surface 100 of the catheter. As in FIG. 5, the projections on the stylet are wedge shaped and the abutment surfaces on both the stylet and the catheter are slanted forwardly as they extend outwardly so that the abutment surfaces have a barb-like cooperation when they engage with each other. It will be noted that the abutment surfaces 104 and 108 on the stylet are much more widely separated than the corresponding abutment surfaces 96 and 100 on the catheter, as in the FIG. 4 embodiment; it will also be noted that the annular recess 98 has a uniform diameter over the length of this recess, and the reason for both of these details of construction will be made clear hereinbelow. As with the FIG. 4 embodiment, if for any reason the forward abutment surface 104 on the stylet should slip past the forward abutment wall 96 on the catheter, the rearward abutment surface 108 on the stylet will engage the rearward abutment surface 100 on the catheter after the stylet has moved forwardly within the catheter a distance equal to the space between the rearward abutment surface 108 on the stylet and the rearward abutment surface 100 on the catheter, thereby providing the same added measure of safety as discussed above in connection with the FIG. 4 embodiment. Again it should be noted that the rearward abutment surface 100 on the cannula is located substantially at the widest part of the gradually widening portion 34 of the cannula and the forward abutment surface 96 is located within the gradually widening portion 34 so that only the gradually widening portion of the cannula is pushed ahead of the abutment means during insertion of the cannula regardless of which of the above described pairs of abutment surfaces are in engagement with each other.

The present invention provides two unique advantages over any known prior art catheters which advantages are derived from the construction of the embodiments described above and will be more apparent from a description to follow of the manner in which the catheter is used in connection with the insertion and retention of the catheter in the bladder. Both of these advantages result from the manner in which the inflatable balloon operates to cause a certain amount of expansion of the distal end of the cannula thereby widening the opening into the drainage lumen and also, in the plural abutment means of the FIG. 4 and FIG. 6 embodiments, allowing a certain degree of freedom of movement of the stylet within the catheter to provide an indication that the balloon has in fact inflated in the bladder and is retaining the catheter in place.

With reference to the embodiments shown in FIGS. 1 and 5, the construction and connection of the inflatable balloon 36, which is the same in both embodiments, causes a certain amount of expansion of the opening 30 at the distal end of the cannula, thus providing a wider opening into the drainage lumen to facilitate drainage of waste material over a larger area. This expansion results from the forward connection 40 of the balloon 36 to the inner layer 22 of the cannula which causes the balloon to exert a strong radial pull on the end of the inner layer. Since the relatively stronger intermediate layer 20 gradually tapers to practically nothing at the end of the cannula, or may terminate altogether before the end of the cannula, this layer offers little or no resistance to the expansion of the forward end of the cannula. As seen in FIG. 7, when the balloon has been fully inflated, the gradually widening portion 34 of the cannula is flared outwardly from approximately the widest part of the gradually widening portion 34 to the end thereof. By providing the other juncture 38 of the balloon 36 with the outer layer 18 of the cannula at the widest point of the gradually widening portion 34, only that portion 34 of the cannula need be inside the bladder thereby maintaining the balloon relatively flat and the opening 30 as low as possible in the bladder thus promoting maximum drainage of waste material from the bladder.

In the embodiments of the invention shown in FIGS. 4 and 6, the expansion effect is enhanced by the construction of the inner layer 22 of the cannula, and in this form of the invention the stylet is utilized to provide an indication that the balloon has inflated. It will be observed that in both of these embodiments the inner layer 22 is thinner in cross-section at least at the location of the rearward abutment surfaces than it is along that portion of the layer 22 within the gradual widening portion 34 of the cannula. The effect of this, as best seen in FIG. 8, is to provide an effective hinge portion of the inner layer about which all three layers of the cannula can bend in response to the radial force exerted on the forward end of the cannula at the terminal portion 40 of the balloon 36. In these two embodiments, the tapered portion 34 of the cannula bends outwardly far enough to cause the forward abutment surfaces on the cannula to disengage from the forward abutment surfaces on the stylet after the balloon is inflated, thereby allowing the stylet to move forwardly in the cannula until the rearward abutment surfaces on the stylet engage with the rearward abutment surfaces on the cannula. This limited movement of the stylet, which will be relatively free movement in both forward and backward directions, provides a positive indication to the person inserting the catheter that the balloon 36 has in fact inflated within the bladder and that there are no leaks in the balloon or other reason present which would prevent inflation of the balloon.

What is claimed is:

1. A retention drainage catheter adapted to be inserted into and retained in the bladder for the continuous drainage of waste material therefrom, said catheter comprising:

A. an elongate cannula formed of a flexible and pliant material and having both distal and proximal ends, the length of said cannula being such that said distal end is disposed within the bladder and the proximal end is disposed exteriorily of the urethra,
   B. said cannula having an inner tubular wall surface defining a drainage lumen which extends from said distal end of said cannula substantially to said proximal end thereof, said cannula being tapered adjacent said distal end thereof to form a gradually widening portion from said distal end to facilitate passage of said cannula through the urethra, said tapered portion of said cannula commencing at said distal end and extending toward said proximal end of said cannula,
   C. said distal end of said cannula defining an unobstructed opening the cross-sectional area of which is substantially equal to the cross-sectional area of said drainage lumen and which lies in a plane substantially perpendicular to the longitudinal axis of said drainage lumen so as to communicate the interior of the bladder directly with the full cross-sectional area of said drainage lumen at said distal end of said cannula whereby waste material in the bladder flows directly into said drainage lumen at said distal end of said cannula and instrumentation is introduced into the bladder through said drainage lumen,
   D. means formed on said inner tubular wall surface adjacent to but spaced from said distal end of said cannula and defining a portion of said drainage lumen of different diameter than the diameter of the rest of said drainage lumen thereby forming an abutment means for a stylet used to insert said catheter, and
   E. expandable means connected to the outer wall surface of said cannula adjacent said distal end thereof for retaining said distal end within the bladder after passing through the urethra, said expandable means comprising an inflatable balloon surrounding said cannula adjacent said distal end thereof, said inflatable balloon being defined by an outer layer of flexible material connected to said distal end of said cannula and to a portion of said cannula spaced from said distal end but being otherwise unconnected thereto, said portion of said cannula being located at least as far from said distal end of said cannula as the widest portion of said gradually widening portion of said cannula so that said inflatable balloon extends at least over the length of said gradually widening portion.

2. A retention drainage catheter as set forth in claim 1 wherein said cannula is tapered adjacent said distal end thereof to form a gradually widening portion from said distal end to facilitate passage of said cannula through the urethra, said tapered portion of said cannula commencing at said plane and extending toward said proximal end of said cannula.

3. A retention drainage catheter adapted to be inserted into and retained in the bladder for the continuous drainage of waste material therefrom, said catheter comprising:

A. an elongate cannula formed of a flexible and pliant material and having both distal and proximal ends, the length of said cannula being such that said distal end is disposed within the bladder and the proximal end is disposed exteriorily of the urethra,
   B. said cannula having an inner tubular wall surface defining a drainage lumen which extends from said distal end of said cannula substantially to said proximal end thereof, said cannula being tapered adjacent said distal end thereof to form a gradually widening portion from said distal end to facilitate passage of said cannula through the urethra, said tapered portion of said cannula commencing at said distal end and extending toward said proximal end of said cannula, C. said distal end of said cannula defining an unobstructed opening the cross-sectional area of which is substantially equal to the cross-sectional area of said drainage lumen and which lies in a plane substantially perpendicular to the longitudinal axis of said drainage lumen so as to communicate the interior of the bladder directly with the full cross-sectional area of said drainage lumen at said distal end of said cannula whereby waste material in the bladder flows directly into said drainage lumen at said distal end of said cannula and instrumentation is introduced into the bladder through said drainage lumen, D. means formed on said inner tubular wall surface adjacent to but spaced from said distal end of said cannula and defining a portion of said drainage lumen of different diameter than the diameter of the rest of said drainage lumen thereby forming an abutment means for a stylet used to insert said catheter, said means forming said abutment means on said inner tubular wall surface comprising an annular boss projecting radially inwardly of said drainage lumen, said annular boss being located adjacent the widest point of said gradually widening portion so that only said gradually widening portion of said cannula is pushed ahead of said abutment means during insertion of the catheter through the urethra, and E. expandable means connected to the outer wall surface of said cannula adjacent said distal end thereof for retaining said distal end within the bladder after passing through the urethra.

* * * * *